Figure 1:
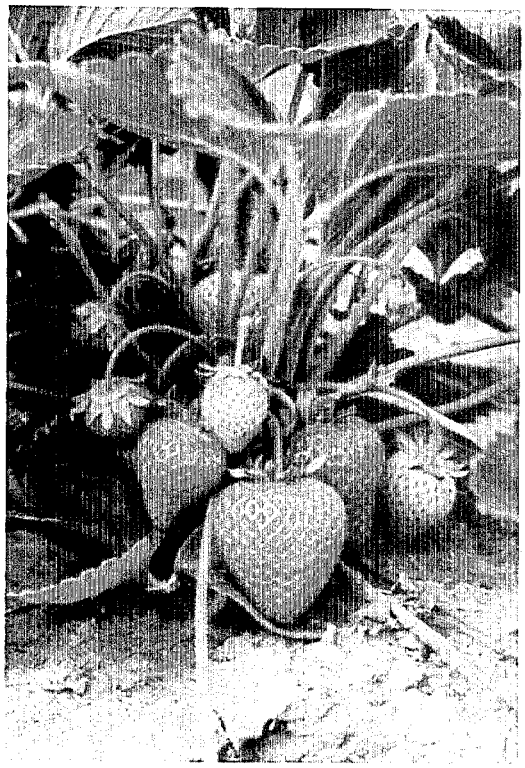

US00PP09310P

United States Patent [19]

Moore

[11] Patent Number: Plant 9,310

[45] Date of Patent: Oct. 3, 1995

[54] STRAWBERRY PLANT 'PUGET RELIANCE'

[75] Inventor: Patrick P. Moore, Puyallup, Wash.

[73] Assignee: Washington State University Research Foundation, Pullman, Wash.

[21] Appl. No.: 304,343

[22] Filed: Sep. 12, 1994

[51] Int. Cl.[6] ..... A01H 5/00

[52] U.S. Cl. ..... Plt./48

[58] Field of Search ..... Plt./48

*Primary Examiner*—James R. Feyrer

*Attorney, Agent, or Firm*—Townsend and Townsend Khourie and Crew

[57] ABSTRACT

'Puget Reliance' is large fruited, high yielding, medium red strawberry suited to processing that is very virus tolerant and moderately cold hardy, producing fruit at the same time as 'Totem'.

2 Drawing Sheets

DESCRIPTION

This invention relates to a new and distinct short day, June bearing variety of strawberry plant named 'Puget Reliance' which is a result of a cross of non-patented selections BC 72-2-72 and WSU 1945. The variety is botanically identified as *F.×annanassa* Duch.

The seedlings resulting from the aforementioned cross were grown asexually by stolen runners in observation plots at WSU Puyallup, Wash. The genealogy of 'Puget Reliance' is shown below in FIG. 3.

The cross was made in an attempt to develop a virus tolerant and aphid resistant cultivar. 'Puget Reliance' was inoculated with a virus complex in the greenhouse prior to planting in the field and evaluated for aphid resistance in 1985 at the Washington State University (WSU) Vancouver Research and Extension Unit. The parent, 'WSU 1945', was known as an aphid resistant selection. In the first evaluation of 'Puget Reliance' the selection was considered aphid resistant. However, later evaluations disclosed that the selection was not aphid resistant but extremely virus tolerant, equal to or exceeding any Pacific Northwest cultivar.

As a sufficient number of plants for replication tests was not available earlier, 'Puget Reliance' was not planted until 1989. This planting was harvested in 1990 and 1991 and had the highest two-year yield, the largest fruit and the lowest preharvest fruit rot of comparable varieties as is shown in Tables 1 and 2 below.

TABLE 1

1990 harvest of 1989 planted strawberries at WSU Puyallup.

| | TOTAL YIELD (t/a) | HIGH PICK (t/a) | FRUIT ROT (%) |
|---|---|---|---|
| 'PUGET RELIANCE' | 16.6 a | 7.0 a | 11.9 qr |
| WSU 2187 | 14.2 ab | 6.9 ab | 28.0 d–n |
| ORUS 965-46 | 12.4 bc | 5.5 a–f | 33.6 a–i |
| BC 76-26-4 | 12.2 b–d | 4.8 a–i | 44.1 a |
| WSU 1980 | 11.6 b–e | 5.5 a–f | 21.6 i–r |
| WSU 2047 | 11.5 b–e | 5.4 a–f | 10.9 r |
| WSU 1998 | 11.5 b–e | 5.9 a–e | 37.9 a–e |
| WSU 1973 | 11.2 b–f | 4.4 c–j | 15.9 n–r |
| SUMAS | 11.1 b–f | 5.5 a–f | 23.3 g–r |
| WSU 2174 | 10.9 b–g | 4.9 a–h | 17.8 k–r |
| REDCREST | 10.7 b–h | 5.5 a–f | 28.1 d–n |
| RAINIER | 10.3 b–i | 4.8 a–i | 32.3 a–j |

TABLE 1-continued 1990 harvest of 1989 planted strawberries at WSU Puyallup.

| | | | |
|---|---|---|---|
| BC 76-26-14 | 10.3 b–i | 5.0 a–g | 35.2 a–h |
| OLYMPUS | 10.2 b–j | 6.1 a–d | 24.2 f–r |
| WSU 2175 | 10.1 b–j | 4.4 c–k | 20.5 i–r |
| WSU 1987 | 10.1 b–j | 6.3 a–c | 30.9 b–k |
| TOTEM | 10.0 b–j | 4.0 c–k | 17.2 l–r |
| WSU 2012 | 9.9 b–j | 5.1 a–g | 30.4 c–l |
| BC 84-16-10 | 9.9 b–k | 5.0 a–g | 30.6 c–l |
| BC 35-14-4 | 9.6 c–k | 4.7 b–i | 27.0 d–o |
| ORUS 980R-185 | 9.3 c–k | 4.8 a–i | 39.3 a–d |
| WSU 2035 | 8.9 c–k | 3.3 f–n | 13.3 p–r |
| WSU 2172 | 8.9 c–k | 3.6 e–m | 36.2 a–g |
| WSU 1971 | 8.9 c–k | 4.6 c–i | 18.0 k–r |
| WSU 2032 | 3.2 c–l | 3.6 e–m | 16.1 n–r |
| BC 84-15-161 | 8.1 c–l | 3.8 d–l | 16.5 m–r |
| HOOD | 8.1 c–l | 3.4 f–n | 27.8 d–n |
| WSU 1972 | 8.1 c–l | 3.9 d–k | 18.8 k–r |
| WSU 2171 | 7.8 d–l | 4.2 c–k | 27.4 d–m |
| SHUSWAP | 7.7 e–l | 3.6 e–m | 42.5 a–c |
| SHUKSAN | 7.6 e–m | 3.6 e–m | 24.9 e–q |
| WSU 2033 | 7.6 e–m | 2.9 g–n | 16.3 m–r |
| WSU 2004 | 7.5 e–m | 3.7 e–m | 29.7 c–l |
| BENTON | 7.3 e–m | 3.4 f–m | 19.8 j–r |
| WSU 1978 | 6.8 f–n | 4.4 c–k | 18.3 k–q |
| WSU 2041 | 6.6 g–n | 3.4 f–n | 22.6 h–r |
| WSU 2176 | 6.3 h–n | 2.5 i–n | 20.5 i–r |
| BC 84-2-3 | 6.0 i–n | 2.6 h–n | 43.1 ab |
| WSU 2180 | 5.9 i–n | 2.5 i–n | 37.4 a–f |
| WSU 2173 | 5.8 j–n | 2.7 h–n | 22.0 h–q |
| WSU 2044 | 5.7 j–n | 2.5 i–n | 13.6 o–r |
| WSU 2188 | 5.4 k–n | 2.0 k–n | 30.9 b–k |
| WSU 2177 | 4.3 l–n | 2.2 k–n | 36.2 a–g |
| WSU 2183 | 4.2 l–n | 1.6 l–n | 25.8 e–p |
| WSU 2185 | 3.3 mn | 1.5 m–n | 21.3 i–r |
| WSU 2181 | 2.7 n | 1.2 n | 37.1 a–f |
| MEAN | 8.7 | 4.1 | 26.0 |

| | FRUIT WEIGHT (g) | FRUIT FIRM-NESS (g) | MIDPOINT OF HARVEST |
|---|---|---|---|
| 'PUGET RELIANCE' | 15.6 a | 223 l–n | 6/23 g–l |
| WSU 2187 | 14.4 ab | 245 j–n | 6/23 h–l |
| ORUS 965-46 | 13.3 a–c | 284 e–l | 6/24 f–j |
| BC 76-26-4 | 14.2 ab | 272 g–m | 6/26 b–f |
| WSU 1980 | 7.3 n–p | 284 e–k | 6/23 i–m |
| WSU 2047 | 8.2 i–p | 257 h–m | 6/24 g–k |
| WSU 1998 | 13.0 a–d | 235 j–n | 6/21 l–o |
| WSU 1973 | 11.8 b–f | 258 h–m | 6/23 h–i |
| SUMAS | 10.3 c–j | 252 i–n | 6/20 m–p |
| WSU 2174 | 11.2 c–h | 340 b–e | 6/24 e–j |
| REDCREST | 10.3 d–l | 362 c–d | 6/27 b–e |
| RAINIER | 10.8 c–k | 238 j–n | 6/24 f–j |
| BC 76-26-14 | 11.8 b–f | 316 d–h | 6/27 b–d |

of the new variety.

Figure 2:
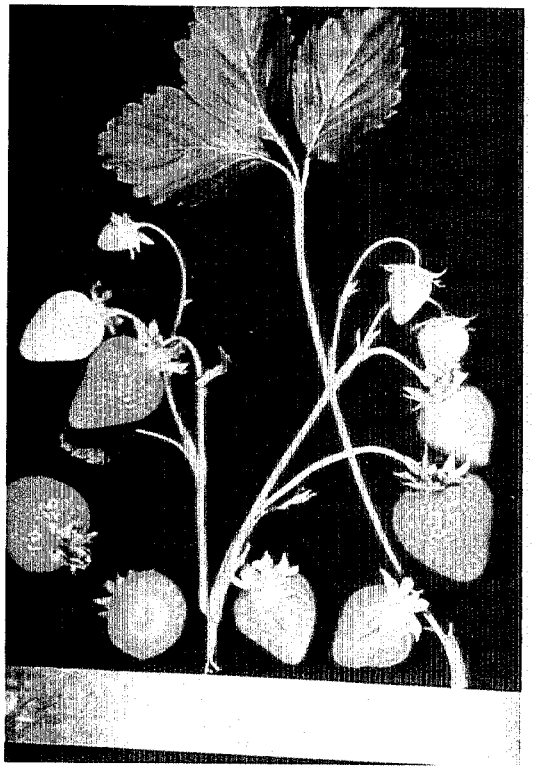

FIG. 2 depicts typical leaf and primary, secondary and tertiary fruit of plants in the first fruiting season (right) and second fruiting season (left) and longitudinal and cross-sections of typical fruit.

Figure 3:
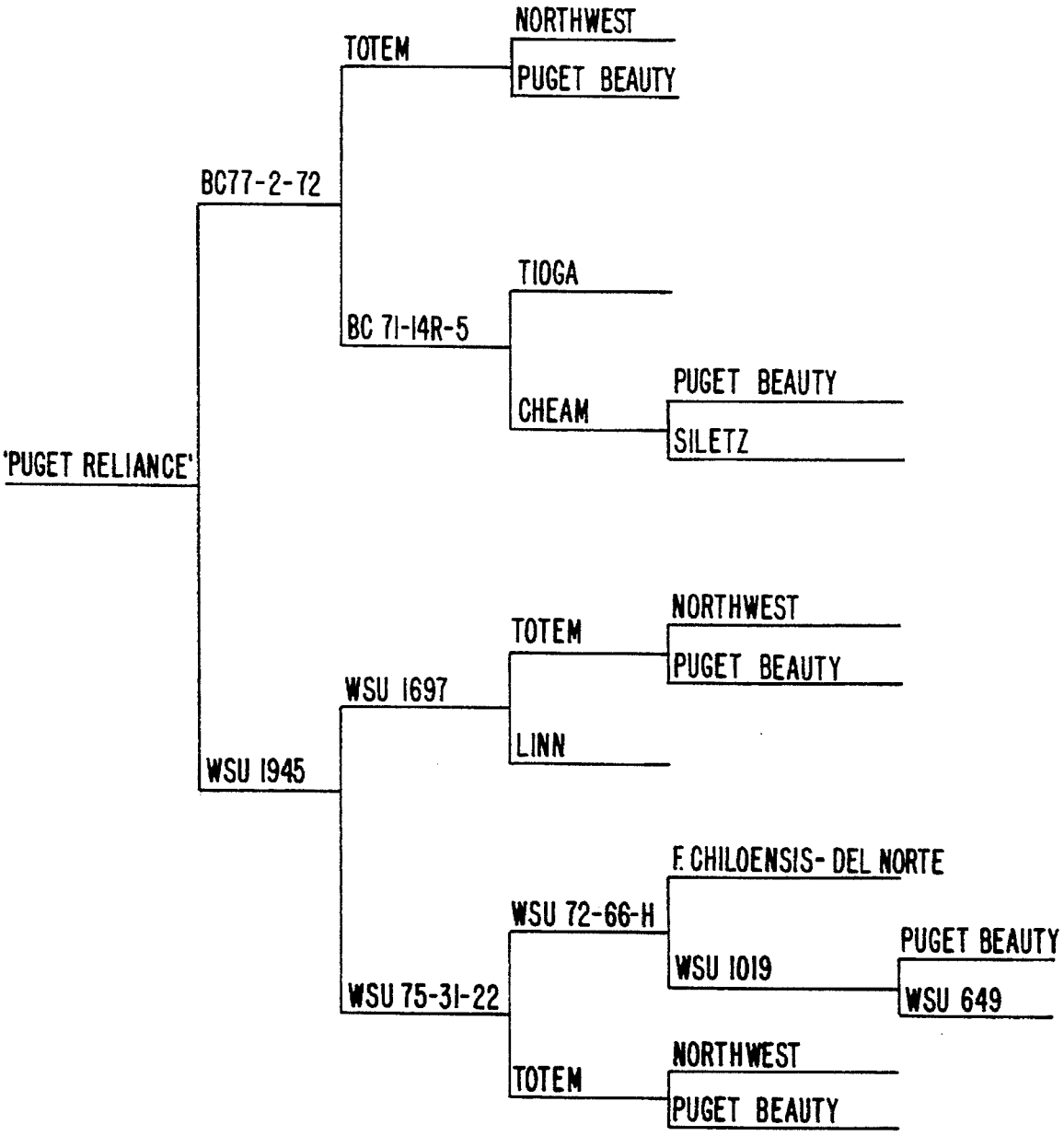

FIG. 3 sets forth the genealogy of 'Puget Reliances'.

The fruit of the new variety is medium red with good internal color and is not as dark as 'Totem' (see Table 15). 'Puget Reliance' was included in a second planting in 1991 and the harvest from that planting in 1992 and 1993 showed it had the highest yield and largest fruit of comparative varieties (see Tables 3 and 4).

TABLE 3

1992 yield of 1991 planted June-bearing strawberries, Puyallup, WA

| Clone | Yield (t/a) | Fruit Rot (%) | Fruit Weight (g) | Fruit Firmness (g) |
|---|---|---|---|---|
| 'PUGET RELIANCE' | 17.6 A | 7% D-E | 15.1 A | 155 C-E |
| WSU 2213 | 15.1 A | 21% A-C | 11.6 B-C | 182 B-D |
| WSU 2212 | 12.5 B | 16% B-D | 9.8 C-D | 183 B-D |
| TOTEM | 12.3 B | 8% D-E | 11.4 B-C | 158 C-E |
| WSU 2122 | 12.0 B | 32% A | 11.1 B-C | 129 E |
| ORUS 4688 | 10.5 B-C | 13% C-E | 9.7 C-D | 178 B-D |
| REDCREST | 10.5 B-C | 13% C-E | 9.8 C-D | 219 B |
| SUMAS | 10.5 B-C | 21% B-C | 8.9 D- | 191 B-C |
| ORUS 1083-135 | 10.3 B-C | 28% A-B | 9.8 C-D | 144 D-E |
| BC 86-27-1 | 8.7 C-D | 23% A-C | 9.5 C-D | 176 B-D |
| MDUS 4740 | 8.6 * | 35% | 13.7 | 204 |
| BC 84-16-10 | 8.3 * | 8% | 8.1 | 219 |
| WSU 2080 | 8.0 C-D | 4% E | 9.5 C-D | 175 B-D |
| BC 86-33-2 | 7.6 C-D | 14% C-E | 8.4 D | 146 D-E |
| WSU 2210 | 7.1 D | 16% B-D | 11.2 B-C | 175 B-D |
| DOUGLAS | 6.4 * | 15% | 9.4 | 142 |
| CAVENDISH | 6.3 * | 22% | 13.5 | 193 |
| ANNAPOLIS | 5.4 * | 7% | 12.4 | 243 |
| PARKER | 5.2 * | 22% | 10.3 | 325 |
| MDUS 4594 | 4.8 * | 24% | 6.5 | 202 |
| MDUS 5120 | 4.0 * | 22% | 10.4 | 257 |
| WSU 2218 | 3.7 E | 21% A-C | 12.6 B | 297 A |
| EARLIGLOW | 3.5 * | 11% | 7.4 | 241 |
| HONEOYE | 3.0 * | 23% | 12.0 | 175 |
| WSU 2219 | 2.8 E | 14% C-E | 5.7 E | 155 C-E |
| BC 86-23-6 | 2.6 E | 23% A-C | 6.4 E | 180 B-D |
| MDUS 4587 | 2.5 * | 2% | 6.3 | 228 |
| MDUS 5149 | 2.0 * | 6% | 6.0 | 185 |
| MDUS 5122 | 1.6 * | 5% | 8.8 | 166 |
| OSO GRANDE | 0.6 * | 14% | 5.8 | 357 |
| Average | 7.1 | 16% | 9.7 | 199 |

| Clone | Harvest Season 5% | 50% | 95% | Length of Season |
|---|---|---|---|---|
| 'PUGET RELIANCE' | 5/27 B-C | 6/5 A-B | 6/15 A-B | 20 A-D |
| WSU 2213 | 5/24 C-E | 6/2 B-C | 6/14 B | 21 A-C |
| WSU 2212 | 5/23 D-E | 5/31 C-D | 6/13 B-C | 21 A-C |
| TOTEM | 5/27 B-C | 6/5 A-B | 6/14 B | 18 C-E |
| WSU 2122 | 5/24 C-E | 6/3 B-C | 6/14 B | 21 A-C |
| ORUS 4688 | 5/31 A | 6/6 A | 6/16 A-B | 16 D-E |
| REDCREST | 5/27 B-C | 6/7 A | 6/18 A | 22 A-B |
| SUMAS | 5/28 B | 6/3 B-C | 6/13 B-C | 16 D-E |
| ORUS 1083-135 | 5/22 E | 5/30 D | 6/11 C-D | 20 A-C |
| BC 86-27-1 | 5/24 C-E | 6/3 B-C | 6/13 B-C | 20 A-D |
| MDUS 4740 | 6/2 | 6/10 | 6/23 | 21 |
| BC 84-16-10 | 5/25 | 6/1 | 6/12 | 18 |
| WSU 2080 | 5/27 B-C | 6/5 A-B | 6/15 B | 19 B-E |
| BC 86-33-2 | 5/27 B-C | 6/5 A-B | 6/14 B | 18 B-E |
| WSU 2210 | 5/22 E | 5/30 D | 6/10 D | 15 E |
| DOUGLAS | 5/21 | 5/30 | 6/12 | 22 |
| CAVENDISH | 5/23 | 5/31 | 6/13 | 21 |

TABLE 3-continued 1992 yield of 1991 planted June-bearing strawberries, Puyallup, WA

| | | | | |
|---|---|---|---|---|
| ANNAPOLIS | 5/20 | 5/27 | 6/5 | 16 |
| PARKER | 5/21 | 6/1 | 6/14 | 24 |
| MDUS 4594 | 5/26 | 6/5 | 6/13 | 18 |
| MDUS 5120 | 5/22 | 5/30 | 6/13 | 22 |
| WSU 2218 | 5/26 B-D | 6/2 B-C | 6/14 B | 19 A-D |
| EARLIGLOW | — | — | 6/9 | |
| HONEOYE | — | 5/25 | 6/8 | |
| WSU 2219 | 5/23 E | 5/29 D | 6/9 D | 17 C-E |
| BC 86-23-6 | 5/26 B-D | 6/2 B-C | 6/18 A | 23 A |
| MDUS 4587 | — | 5/26 | 6/8 | |
| MDUS 5149 | — | 5/28 | 6/9 | |
| MDUS 5122 | — | 5/24 | 6/8 | |
| OSO GRANDE | — | 5/27 | 6/13 | |
| Average | 5/25 | 6/1 | 6/12 | 20 |

Means followed by letters are averages of three 10 foot plots.
Means not followed by letters are based on a single 10 foot plot.
Means within columns followed by the same letter are not significantly different using Duncan's Multiple Range Test, P = 0.05.

TABLE 4

1992-93 harvests of 1991 planted strawberries at Puyallup, WA.

| | Yield (t/a) 1993 | | 1992 | total | Fruit weight (g) | |
|---|---|---|---|---|---|---|
| 'PUGET RELIANCE' | 10.6 | A | 17.6 | 28.2 | 11.6 | A |
| TOTEM | 8.0 | A-B | 12.3 | 20.3 | 6.8 | B-C |
| WSU 2213 | 4.5 | B | 15.1 | 19.7 | 8.4 | B |
| BOUNTIFUL | 8.0 | A-B | 10.5 | 18.5 | 7.1 | B-C |
| ORUS 1083-135 | 8.1 | A-B | 10.3 | 18.4 | 9.0 | B |
| SUMAS | 7.6 | A-B | 10.5 | 18.1 | 8.7 | B |
| WSU 2212 | 5.2 | B | 12.5 | 17.7 | 6.9 | B-C |
| WSU 2122 | 5.5 | B | 12.0 | 17.4 | 8.5 | B |
| REDCREST | 3.8 | B | 10.5 | 14.3 | 5.4 | C |
| BC 86-33-2 | 4.2 | B | 7.6 | 11.9 | 6.6 | B-C |
| Average | 6.5 | | 11.9 | 18.5 | 7.9 | |

| | Fruit firmness (g) | Fruit rot (%) | | Midpoint of harvest | |
|---|---|---|---|---|---|
| 'PUGET RELIANCE' | 201 A | 55.4 | A-C | 6/13 | B-C |
| TOTEM | 220 A | 30.9 | D | 6/16 | A-B |
| WSU 2213 | 201 A | 42.3 | C-D | 6/16 | A-B |
| BOUNTIFUL | 175 A | 33.1 | D | 6/16 | A |
| ORUS 1083-135 | 192 A | 59.1 | A-B | 6/10 | D-E |
| SUMAS | 218 A | 39.2 | C-D | 6/10 | D-E |
| WSU 2212 | 183 A | 52.3 | A-C | 6/15 | A-C |
| WSU 2122 | 183 A | 66.4 | A | 6/9 | E |
| REDCREST | 199 A | 44.0 | B-D | 6/14 | A-C |
| BC 86-33-2 | 174 A | 33.6 | D | 6/13 | C-D |
| Average | 195 | 45.6 | | 6/13 | |

Means followed by the same letter are not significantly different using Duncan's Multiple Range Test, P = 0.05.

In plantings established at Puyallup and Mt. Vernon, Wash. in 1992 the yields were less than in previous tests. However, they were not significantly different than the highest yielding clones (see Tables 5 and 6).

TABLE 5

1993 harvest of 1992 planted strawberries at Puyallup, WA.

| | Yield (t/a) | Fruit weight (g) | Fruit firmness (g) |
|---|---|---|---|
| ORUS 4817 | 17.3 | 9.2 | 236 |

TABLE 5-continued 1993 harvest of 1992 planted strawberries at Puyallup, WA.

| | | | | | | |
|---|---|---|---|---|---|---|
| REDGEM | 15.5 | | 9.8 | | 220 | |
| HONEOYE | 13.6 | | 12.3 | | 231 | |
| BC 86-27-1 | 12.8 | A | 12.1 | C-F | 192 | F-I |
| BC 86-33-2 | 12.7 | A-B | 13.6 | A-C | 211 | D-I |
| SUMAS | 12.4 | A-B | 12.1 | C-F | 227 | C-H |
| BC 86-30-56 | 12.3 | A-B | 13.5 | A-D | 205 | F-I |
| 'PUGET RELIANCE' | 12.0 | | 16.9 | | 274 | |
| 'PUGET RELIANCE'-VF | 11.9 | A-C | 16.3 | A | 240 | C-G |
| WSU 2006 | 11.7 | A-D | 11.0 | C-G | 176 | G-I |
| WSU 2169 | 11.5 | | 11.0 | | 283 | |
| BC 86-22-33 | 11.3 | A-D | 15.4 | A-B | 228 | C-H |
| BC 84-15-161 | 11.1 | A-D | 10.1 | E-H | 251 | C-G |
| CAVENDISH | 10.8 | A-D | 15.2 | A-B | 248 | C-G |
| BC 84-16-10 | 10.7 | A-D | 11.9 | C-F | 199 | F-I |
| RAINIER | 9.9 | A-E | 11.2 | C-G | 278 | B-F |
| ORUS 1083-135 | 9.8 | A-E | 10.0 | E-H | 229 | C-H |
| TOTEM | 9.8 | A-E | 12.0 | C-F | 244 | C-G |
| BOUNTIFUL | 9.1 | A-F | 11.8 | C-G | 144 | H-I |
| BC 85-13-14 | 8.6 | A-G | 7.2 | H | 134 | I |
| WSU 2187 | 8.4 | A-G | 12.5 | B-E | 210 | D-I |
| WSU 2077 | 8.2 | A-G | 12.1 | C-F | 260 | B-G |
| BENTON | 8.0 | A-H | 8.6 | G-H | 201 | F-I |
| WSU 2244 | 7.8 | A-H | 8.9 | F-H | 248 | C-G |
| REDCREST | 7.7 | B-H | 10.4 | D-G | 317 | B-C |
| VEESTAR | 7.0 | | 9.5 | | 182 | |
| BC 86-22-9 | 7.0 | C-H | 11.5 | C-G | 214 | D-I |
| SHUKSAN | 6.8 | D-H | 11.1 | C-G | 206 | E-I |
| ORUS 4357 | 6.4 | | 9.9 | | 202 | |
| R8607-2 | 6.0 | | 9.5 | | 253 | |
| WSU 2133E | 5.7 | E-H | 12.6 | B-E | 236 | C-G |
| WSU 2229E | 5.6 | | 11.7 | | 155 | |
| SENECA | 5.5 | E-H | 12.1 | C-F | 465 | A |
| HOOD | 5.1 | E-H | 8.7 | G-H | 266 | B-G |
| WSU 2143E | 5.1 | E-H | 9.1 | F-H | 195 | F-I |
| TOKLAT | 5.0 | | 5.0 | | 137 | |
| R8614-2 | 4.9 | | 7.4 | | 218 | |
| WSU 2139E | 4.6 | F-H | 12.5 | B-E | 302 | B-D |
| NY 1593 | 4.1 | H-I | 9.1 | F-H | 343 | B |
| WSU 2106E | 3.9 | | 9.7 | | 271 | |
| MD 4589 | 3.9 | | 8.5 | | 423 | |
| R8713-8 | 3.6 | | 14.5 | | 342 | |
| WSU 2140E | 3.2 | H-I | 9.2 | F-H | 298 | B-E |
| BEAVER BELLE | 2.6 | | 9.7 | | 259 | |
| R8614-3 | 1.7 | | 5.5 | | 249 | |
| BEAVER SWEET | 0.7 | | — | | — | |
| WSU 2086E | 0.4 | | 6.5 | | 134 | |
| WSU 2089E | 0.1 | | 3.6 | | 140 | H-I |
| Average | 7.8 | | 10.7 | | 238 | |

| | Fruit rot (%) | | Midpoint of harvest | |
|---|---|---|---|---|
| ORUS 4817 | 22 | | 6/15 | |
| REDGEM | 46 | | 6/15 | |
| HONEOYE | 48 | | 6/5 | |
| BC 86-27-1 | 34 | G-J | 6/13 | D-G |
| BC 86-33-2 | 32 | H-J | 6/11 | E-H |
| SUMAS | 36 | G-J | 6/11 | F-I |
| BC 86-30-56 | 62 | A-E | 6/15 | B-D |
| 'PUGET RELIANCE' | 86 | | 6/8 | |
| 'PUGET RELIANCE '-VF | 53 | C-G | 6/10 | G-I |
| WSU 2006 | 31 | H-J | 6/15 | B-D |
| WSU 2169 | 61 | | 6/12 | |
| BC 86-22-33 | 49 | D-I | 6/13 | D-G |
| BC 84-15-161 | 19 | J | 6/20 | A |
| CAVENDISH | 73 | A-B | 6/10 | H-K |
| BC 84-16-10 | 47 | D-I | 6/14 | B-E |
| RAINIER | 72 | A-C | — | |
| ORUS 1083-135 | 64 | A-D | 6/10 | H-J |
| TOTEM | 56 | B-F | 6/12 | E-H |
| BOUNTIFUL | 46 | D-I | 6/16 | B |
| BC 85-13-14 | 44 | E-I | 6/16 | |
| WSU 2187 | 47 | D-I | 6/15 | B-D |
| WSU 2077 | 68 | A-C | 6/11 | F-I |
| BENTON | 29 | I-J | 6/16 | B-C |

TABLE 5-continued 1993 harvest of 1992 planted strawberries at Puyallup, WA.

| | | | | |
|---|---|---|---|---|
| WSU 2244 | 47 | D-I | 6/7 | K |
| REDCREST | 57 | A-F | 6/13 | C-F |
| VEESTAR | 54 | | 6/4 | |
| BC 86-22-9 | 46 | D-I | 6/8 | |
| SHUKSAN | 42 | F-I | 6/14 | B-E |
| ORUS 4357 | 51 | | 6/13 | |
| R8607-2 | 57 | | — | |
| WSU 2133E | 64 | A-D | 6/10 | |
| WSU 2229E | 54 | | 6/17 | |
| SENECA | 73 | A-B | 6/7 | J-K |
| HOOD | 49 | D-H | 6/8 | I-K |
| WSU 2143E | 62 | A-E | 6/10 | H-K |
| TOKLAT | 83 | | — | |
| R8614-2 | 71 | | 6/6 | |
| WSU 2139E | 68 | A-C | 6/10 | |
| NY 1593 | 76 | A | — | |
| WSU 2106E | 57 | | 6/9 | |
| MD 4589 | 71 | | — | |
| R8713-8 | 70 | | — | |
| WSU 2140E | 64 | A-D | 6/7 | |
| BEAVER BELLE | 73 | | — | |
| R8614-3 | 62 | | — | |
| BEAVER SWEET | 98 | | 6/8 | |
| WSU 2086E | 33 | | — | |
| WSU 2089E | 29 | H-J | — | |
| Average | 55 | | 6/11 | |

Means followed by the same letter are not significantly different using Duncan's Multiple Range Test, P = 0.05.
Numbers in bold represent means of three 10 foot plots, light print represents means of one or two 10 foot plots and were not included in the statistical analysis.

TABLE 6

1993 harvests of 1992 planted strawberries at Mt. Vernon, WA.

| | Yield (t/a) | | Fruit weight (g) | | Fruit rot (%) | |
|---|---|---|---|---|---|---|
| BOUNTIFUL | 14.4 | A | 13.4 | B-E | 20.3 | D-H |
| SUMAS | 13.4 | A-B | 13.3 | B-E | 28.7 | B-H |
| 'PUGET RELIANCE' | 13.2 | A-B | 13.2 | B-F | 14.0 | H |
| 'PUGET RELIANCE'-VF | 12.5 | A-B | 15.0 | A-C | 16.0 | F-H |
| ORUS 1083-135 | 11.1 | A-C | 12.0 | C-G | 36.0 | B-C |
| REDCREST | 11.0 | A-D | 12.6 | B-F | 16.0 | F-H |
| BC 86-22-23 | 10.7 | A-D | 14.0 | B-D | 17.0 | E-H |
| BC 84-16-10 | 10.1 | A-D | 12.7 | B-F | 18.0 | E-H |
| HOOD | 9.5 | A-E | 11.2 | D-H | 31.7 | B-E |
| BC 86-30-56 | 9.1 | B-F | 17.1 | A | 18.7 | E-H |
| HONEOYE | 8.9 | B-G | 12.9 | B-F | 22.3 | C-H |
| BC 86-33-2 | 8.6 | B-G | 13.9 | B-D | 18.0 | B-H |
| BC 86-22-9 | 8.1 | B-H | 10.6 | B-H | 14.0 | H |
| RAINIER | 8.1 | B-H | 15.3 | A-B | 21.7 | C-H |
| NY 1593 | 6.7 | C-I | 13.0 | B-F | 41.7 | B |
| BENTON | 6.2 | C-J | 8.7 | H-I | 14.0 | H |
| CAVENDISH | 5.9 | C-J | 15.0 | A-C | 15.3 | G-H |
| SHUKSAN | 5.8 | C-J | 12.0 | C-G | 20.0 | D-H |
| BC 84-15-161 | 5.6 | D-J | 10.1 | F-H | 13.0 | H |
| EC 85-13-14 | 4.3 | E-J | 9.3 | G-H | 22.3 | C-H |
| BC 86-27-1 | 4.0 | F-J | 11.3 | D-H | 13.0 | H |
| TOTEM | 4.0 | F-J | 10.3 | E-H | 30.0 | B-G |
| WSU 2187 | 3.6 | G-J | 10.3 | E-H | 26.7 | C-H |
| WSU 2068 | 3.1 | H-J | 8.8 | H-I | 24.7 | C-H |
| SENECA | 1.6 | I-J | 8.3 | H-I | 31.3 | B-F |
| GLOOSCAP | 1.5 | I-J | 6.2 | I-J | 34.7 | B-D |
| TOKLAT | 1.3 | J | 5.4 | J | 65.0 | A |
| Average | 7.5 | | 11.7 | | 23.9 | |

| | Midpoint of Harvest | | Stand establishment (%) |
|---|---|---|---|

TABLE 6-continued 1993 harvests of 1992 planted strawberries at Mt. Vernon, WA.

| | | | | |
|---|---|---|---|---|
| BOUNTIFUL | 6/13 | B-D | 100 | A |
| SUMAS | 6/8 | G-J | 100 | A |
| 'PUGET RELIANCE' | 6/11 | C-F | 100 | A |
| 'PUGET RELIANCE'-VF | 6/10 | E-H | 100 | A |
| ORUS 1083-135 | 6/9 | F-J | 100 | A |
| REDCREST | 6/13 | B-D | 100 | A |
| BC 86-22-23 | 6/15 | B | 100 | A |
| BC 84-16-10 | 6/13 | B-D | 100 | A |
| HOOD | 6/11 | C-F | 100 | A |
| BC 86-30-56 | 6/14 | B-C | 100 | A |
| HONEOYE | 6/4 | | 46 | C-D |
| BC 86-33-2 | 6/11 | D-G | 96 | A |
| BC 86-22-9 | 6/7 | I-J | 96 | A |
| RAINIER | 6/4 | | 42 | D |
| NY 1593 | 6/10 | | 92 | A |
| BENTON | 6/14 | B | 92 | A |
| CAVENDISH | 6/8 | H-J | 71 | A-C |
| SHUKSAN | 6/10 | E-I | 71 | A-C |
| BC 84-15-161 | 6/18 | A | 100 | A |
| EC 85-13-14 | 6/12 | B-E | 75 | A-B |
| BC 86-27-1 | 6/6 | J | 75 | A-B |
| TOTEM | 6/9 | F-J | 96 | A |
| WSU 2187 | 6/10 | E-H | 92 | A |
| WSU 2068 | 6/10 | E-H | 88 | A |
| SENECA | 6/3 | K | 59 | B-D |
| GLOOSCAP | 6/8 | G-J | 79 | A-B |
| TOKLAT | 6/2 | | 92 | A |
| Average | 6/10 | | 87 | |

Means are averages of three 10 foot plots.
Means within columns followed by the same letter are not significantly different using Duncan's Multiple Range Test, P = 0.05.

The plants in the last two plantings were in poor physiological condition and in an effort to produce as many plants as possible for testing in 1992, the plants were placed in a heated, lighted greenhouse to produce runners. Possibly because of lack of chilling these plants did not produce runners and at planting time the plants were large and woody and in poor condition. Nonetheless, they performed well and were not significantly lower yielding than the highest yielding clones. At both locations plants which were virus negative were planted. There were no differences between the virus infected plants and the virus negative plants. Accordingly, 'Puget Reliance' appears to be extremely virus tolerant.

Subsequently, the new variety was tested by Oregon State University at Aurora, Ore. and by Agriculture Canada at Abbotsford, British Columbia.

In 1992 a single unreplicated plot of 'Puget Reliance' was the highest yielding clone at Aurora. The variety was rated as one of the best for fruit quality at Abbotsford. However, it displayed susceptibility to post-harvest fruit rot. To date the variety has not been tested for resistance to specific races of red stele but it performed well at Mt. Vernon on non-fumigated land.

In test plantings established at Puyallup from 1989 to 1992 with virus infected plants, the new variety outperformed two of the most widely grown Pacific Northwest cultivars, 'Totem' and 'Sumas'.

'Puget Reliances' outyielded 'Totem' by 39% in its first harvest season and by 31% in its second season. It outyielded 'Sumas' by 31% in the first harvest season and by 30% in the second harvest season. In the same plantings 'Puget Reliance' had fruit which was 36% larger than 'Totem' in the first season and 57% larger in the second season. Its fruit was 47% larger than 'Sumas' in the first season and 30% larger in the second season.

Table 7 is a summary of the 1994 harvest season data. As seen from the table, 'Puget Reliance' clearly had superior yield and fruit size compared to other cultivars.

TABLE 7

1994 yield of 1993 planted strawberries, Puyallup, WA.

| | Marketable yield (t/a) | rot yield (t/a) | Total yield (t/a) | percent Fruit Rot | Fruit Weight (g) | Fruit Firmness (g) |
|---|---|---|---|---|---|---|
| 'PUGET RELIANCE' | 17.5 | 5.9 | 23.4 | 25% | 17.0 | 213 |
| BENTON | 12.1 | 5.3 | 17.4 | 31% | 12.7 | 181 |
| ORUS917-123 | 12.7 | 4.5 | 17.2 | 26% | 10.4 | 289 |
| ORUS1077-47 | 12.1 | 4.0 | 16.2 | 25% | 17.3 | 253 |
| WSU 2211 | 8.1 | 7.8 | 15.9 | 49% | 20.6 | 194 |
| TOTEM | 10.0 | 5.3 | 15.3 | 34% | 12.4 | 234 |
| RAINIER | 8.9 | 6.4 | 15.3 | 42% | 15.1 | 233 |
| REDGEM | 8.9 | 5.7 | 14.5 | 39% | 11.9 | 195 |
| SUMAS | 7.1 | 7.4 | 14.5 | 52% | 15.1 | 227 |
| WSU 2225 | 8.9 | 5.5 | 14.4 | 38% | 11.9 | 201 |
| BC 86-27-1 | 9.0 | 5.3 | 14.2 | 37% | 12.7 | 291 |
| WSU 2253A | 8.7 | 3.7 | 12.4 | 32% | 15.3 | 311 |
| WSU 2170 | 8.0 | 3.5 | 11.5 | 30% | 8.9 | 233 |
| REDCREST | 7.2 | 4.1 | 11.4 | 37% | 9.3 | 296 |
| WSU 2265 | 7.6 | 3.4 | 11.0 | 33% | 12.5 | 253 |
| MELODY | 6.9 | 3.7 | 10.6 | 35% | 9.7 | 244 |
| SHUKSAN | 5.7 | 4.6 | 10.3 | 45% | 12.5 | 239 |
| WSU 2241 | 2.6 | 6.7 | 9.4 | 73% | 17.0 | 285 |
| WSU 2081 | 2.6 | 6.5 | 9.1 | 71% | 13.4 | 164 |
| BC 86-33-2 | 4.3 | 4.6 | 8.9 | 47% | 10.9 | 266 |
| WSU 2076 | 5.3 | 3.6 | 8.9 | 40% | 13.7 | 246 |
| WSU 2260 | 5.1 | 3.4 | 8.4 | 40% | 12.7 | 329 |
| WSU 1983 | 4.1 | 4.1 | 8.2 | 52% | 15.2 | 274 |
| WSU 2235 | 4.3 | 3.7 | 8.0 | 47% | 13.4 | 228 |
| HOOD | 5.2 | 2.2 | 7.4 | 28% | 11.3 | 237 |
| WSU 2239 | 3.9 | 2.6 | 6.5 | 40% | 14.8 | 192 |
| EVITA | 3.5 | 2.9 | 6.3 | 42% | 15.3 | 247 |
| BC 89-28-41 | 3.2 | 2.7 | 5.9 | 45% | 8.6 | 325 |
| WSU 2168 | 3.1 | 1.2 | 4.3 | 27% | 5.4 | 207 |

| | Harvest Season | | | |
|---|---|---|---|---|
| | 5% harvest | 50% harvest | 95% harvest | Length of harvest |
| 'PUGET RELIANCE' | 6/4/94 | 6/15/94 | 6/27/94 | 23 |
| BENTON | 6/7/94 | 6/17/94 | 6/30/94 | 23 |
| ORUS917-123 | 6/10/94 | 6/20/94 | 7/2/94 | 22 |
| ORUS1077-47 | 6/10/94 | 6/21/94 | 7/5/94 | 24 |
| WSU 2211 | 6/1/94 | 6/11/94 | 6/23/94 | 22 |
| TOTEM | 6/3/94 | 6/14/94 | 6/28/94 | 25 |
| RAINIER | 6/5/94 | 6/15/94 | 6/29/94 | 24 |
| REDGEM | 6/2/94 | 6/13/94 | 6/27/94 | 25 |
| SUMAS | 6/1/94 | 6/10/94 | 6/23/94 | 22 |
| WSU 2225 | 6/3/94 | 6/14/94 | 6/28/94 | 25 |
| BC 86-27-1 | 6/1/94 | 6/11/94 | 6/26/94 | 25 |
| WSU 2253A | 5/27/94 | 6/9/94 | 6/27/94 | 30 |
| WSU 2170 | 6/5/94 | 6/18/94 | 7/1/94 | 25 |
| REDCREST | 6/3/94 | 6/15/94 | 6/30/94 | 27 |
| WSU 2265 | 5/31/94 | 6/8/94 | 6/21/94 | 21 |
| MELODY | 5/31/94 | 6/9/94 | 6/25/94 | 25 |
| SHUKSAN | 6/5/94 | 6/13/94 | 6/25/94 | 20 |
| WSU 2241 | 6/3/94 | 6/12/94 | 6/28/94 | 25 |
| WSU 2081 | 6/1/94 | 6/12/94 | 6/27/94 | 26 |
| BC 86-33-2 | 6/2/94 | 6/12/94 | 6/27/94 | 25 |
| WSU 2076 | 6/4/94 | 6/15/94 | 7/1/94 | 27 |
| WSU 2260 | 6/6/94 | 6/18/94 | 7/2/94 | 26 |
| WSU 1983 | 5/28/94 | 6/7/94 | 6/18/94 | 20 |
| WSU 2235 | 6/3/94 | 6/13/94 | 6/27/94 | 25 |
| HOOD | 5/30/94 | 6/9/94 | 6/23/94 | 23 |
| WSU 2239 | 6/1/94 | 6/12/94 | 6/29/94 | 28 |
| EVITA | 5/25/94 | 6/6/94 | 6/22/94 | 28 |
| BC 89-28-41 | 6/3/94 | 6/16/94 | 6/30/94 | 27 |
| WSU 2168 | 5/30/94 | 6/10/94 | 6/27/94 | 28 |

Although the fruit is large and attractive, its softness and susceptibility to post-harvest fruit rot make it unsuited for most fresh market uses.

The fruit from Puyallup and Aurora was sent to the Food Science and Technology Department of Oregon State University for evaluation in 1992. These evaluations were as (a) fresh fruit, (b) IQF fruit* and (c) frozen sliced fruit. The comparison varieties were 'Totem', three 'ORUS' selections, and one 'Agriculture Canada' selection. These evaluations were reported to the Oregon Strawberry Commission and are set forth in Tables 8 through 10 below.

*"IQF Fruit" means "individual quick frozen fruit" and refers to individual fruit that are frozen whole and packaged after freezing. IQF Fruit are discrete, whole frozen strawberries in contrast to frozen sliced fruit or bulk frozen fruit frozen together in a block.

TABLE 8

(From 1993 progress report to Oregon Strawberry Commission by Brian Yorgey)
Fresh Strawberries, 1992–93 Consumer Panel
Means, Standard Deviations (in parentheses), Least Significant Difference (LSD) and Significance Level for Flavor and Appearance
(Means with the same superscripts within each column are not significantly different: p ≦ .05.)

| | Flavor | | | | |
|---|---|---|---|---|---|
| Selection | Overall Flavor | Sweet-ness | Sour-ness | Straw-berry Flavor | Firm-ness |
| 1076-124 | 4.99$^{b}$ | 5.11$^{c}$ | 4.83$^{b}$ | 5.05$^{c}$ | 5.82 |
| | (1.93) | (1.96) | (1.96) | (2.06) | (1.57) |
| 1267-314 | 5.52$^{b}$ | 5.86$^{b}$ | 5.33$^{b}$ | 5.29$^{bc}$ | 5.26 |
| | (2.08) | (1.66) | (1.78) | (2.07) | (1.92) |
| 1267-236 | 5.42$^{b}$ | 5.42$^{bc}$ | 5.14$^{b}$ | 5.23$^{bc}$ | 5.62 |
| | (1.91) | (1.78) | (1.86) | (2.04) | (1.57) |
| 'PUGET | 3.80$^{c}$ | 4.14$^{d}$ | 4.17$^{c}$ | 4.03$^{d}$ | 5.24 |
| RELIANCE' | (1.81) | (1.56) | (1.64) | (1.95) | (1.79) |
| BC 86-33-2 | 6.52$^{a}$ | 6.62$^{a}$ | 5.97$^{a}$ | 6.33$^{a}$ | 5.77 |
| | (1.83) | (1.62) | (1.81) | (1.93) | (1.81) |
| Totem | 5.44$^{b}$ | 5.77$^{b}$ | 5.26$^{b}$ | 5.79$^{ab}$ | 5.46 |
| | (1.92) | (1.66) | (1.77) | (1.81) | (1.52) |
| LSD | .57 | .53 | .54 | .58 | — |
| Sig. Level | .0001 | .0001 | .0001 | .0001 | NS |

| | Appearance | | | | |
|---|---|---|---|---|---|
| Selection | Overall Appear-rance | Color | Size | Shape | Seedi-ness |
| 1076-124 | 6.47$^{b}$ | 6.72$^{a}$ | 6.68$^{b}$ | 6.35$^{b}$ | 5.88$^{b}$ |
| | (1.73) | (1.48) | (1.60) | (1.89) | (1.55) |
| 1267-314 | 7.17$^{a}$ | 7.07$^{a}$ | 7.46$^{a}$ | 7.15$^{a}$ | 6.53$^{a}$ |
| | (1.40) | (1.47) | (1.28) | (1.32) | (1.38) |
| 1267-236 | 5.76$^{c}$ | 6.11$^{b}$ | 5.89$^{dc}$ | 5.62$^{c}$ | 5.91$^{b}$ |
| | (1.63) | (1.66) | (1.57) | (1.80) | (1.47) |
| 'PUGET | 5.50$^{c}$ | 5.27$^{c}$ | 5.99$^{c}$ | 6.56$^{b}$ | 5.73$^{b}$ |
| RELIANCE' | (1.84) | (2.12) | (1.60) | (1.48) | (1.65) |
| BC 86-33-2 | 5.50$^{c}$ | 5.96$^{b}$ | 5.50$^{d}$ | 5.29$^{c}$ | 5.18$^{c}$ |
| | (1.55) | (1.86) | (1.77) | (1.78) | (1.57) |
| Totem | 6.77$^{ab}$ | 6.70$^{a}$ | 6.79$^{b}$ | 6.74$^{ab}$ | 6.39$^{a}$ |
| | (1.24) | (1.47) | (1.23) | (1.37) | (1.46) |
| LSD | .44 | .49 | .41 | .46 | .40 |
| Sig. Level | .0001 | .0001 | .0001 | .0001 | .0001 |

TABLE 9

(From 1993 progress report to Oregon Strawberry Commission by Brian Yorgey)
IQF Strawberries, 1992–93 Consumer Panel
Means, Standard Deviations (in parentheses), Least Significant Difference (LSD) and Significance Level for Flavor and Appearance
(Means with the same superscripts within each column are not significantly different: p ≦ .05.)

| | Flavor | | | | |
|---|---|---|---|---|---|
| Selection | Overall Flavor | Sweet-ness | Sour-ness | Straw-berry Flavor | Firm-ness |
| 1076-124 | 4.95 | 4.68 | 4.53 | 4.95 | 5.03$^{a}$ |
| | (1.89) | (1.97) | (1.66) | (1.85) | (2.10) |
| 1077-47 | 4.58 | 4.70 | 4.57 | 4.85 | 4.43$^{bc}$ |
| | (1.93) | (1.89) | (1.82) | (1.98) | (1.95) |
| 1267-236 | 4.82 | 4.65 | 4.60 | 4.70 | 4.86$^{ab}$ |
| | (1.75) | (1.71) | (1.69) | (1.72) | (1.95) |
| 'PUGET | 4.58 | 4.35 | 4.42 | 4.44 | 4.61$^{abc}$ |
| RELIANCE' | (2.04) | (1.90) | (1.96) | (2.04) | (1.98) |
| BC 86-33-2 | 4.79 | 4.82 | 4.60 | 4.98 | 4.35$^{c}$ |
| | (1.91) | (1.81) | (1.84) | (1.96) | (2.10) |
| Totem | 4.77 | 4.79 | 4.72 | 4.81 | 4.85$^{ab}$ |
| | (1.95) | (1.84) | (1.69) | (1.88) | (1.96) |
| LSD | — | — | — | — | .48 |
| Sig. Level | NS | NS | NS | NS | .04 |

| | Appearance | | | | |
|---|---|---|---|---|---|
| Selection | Overall Appear-rance | Color | Size | Shape | Seedi-ness |
| 1076-124 | 5.52$^{abc}$ | 5.87$^{c}$ | 5.63$^{c}$ | 5.65$^{bcd}$ | 5.75$^{bc}$ |
| | (1.72) | (1.67) | (1.65) | (1.78) | (1.43) |
| 1077-47 | 6.01$^{a}$ | 6.32$^{a}$ | 6.27$^{a}$ | 5.98$^{abc}$ | 6.20$^{a}$ |
| | (1.52) | (1.51) | (1.48) | (1.90) | (1.41) |
| 1267-236 | 5.49$^{bc}$ | 5.63$^{bc}$ | 5.66$^{bc}$ | 5.52$^{cd}$ | 5.2$^{d}$ |
| | (1.60) | (1.72) | (1.72) | (1.68) | (1.53) |
| 'PUGET | 5.94$^{ab}$ | 5.92$^{ab}$ | 6.11$^{ab}$ | 6.23$^{a}$ | 6.09$^{ab}$ |
| RELIANCE' | (1.70) | (1.67) | (1.59) | (1.67) | (1.55) |
| BC 86-33-2 | 5.05$^{c}$ | 5.38$^{abc}$ | 5.89$^{abc}$ | 5.38$^{d}$ | 5.61$^{cd}$ |
| | (1.97) | (2.05) | (1.63) | (1.95) | (1.51) |
| Totem | 5.70$^{ab}$ | 5.72$^{a}$ | 6.23$^{a}$ | 6.10$^{ab}$ | 6.29$^{a}$ |
| | (1.82) | (1.66) | (1.61) | (1.63) | (1.47) |
| LSD | .50 | .50 | .47 | .51 | .41 |
| Sig. Level | .002 | .01 | .02 | .005 | .0001 |

TABLE 10

(From 1993 progress report to Oregon Strawberry Commission by Brian Yorgey)
Sugared and Sliced Strawberries, 1992–93 Consumer Panel
Means, Standard Deviations (in parentheses), Least Significant Difference (LSD) and Significance Level for Flavor and Appearance
(Means with the same superscripts within each column are not significantly different: p ≦ .05.)

| | Flavor | | | | |
|---|---|---|---|---|---|
| Selection | Overall Flavor | Sweet-ness | Sour-ness | Straw-berry Flavor | Firm-ness |
| 1076-124 | 6.39 | 6.40 | 5.88$^{a}$ | 6.15 | 5.56$^{ab}$ |
| | (1.75) | (1.64) | (1.54) | (1.77) | (2.04) |
| 1077-47 | 6.16 | 6.21 | 5.51$^{b}$ | 5.92 | 5.21$^{bc}$ |
| | (1.60) | (1.58) | (1.48) | (1.76) | (1.59) |
| 1267-236 | 6.35 | 6.55 | 5.98$^{a}$ | 6.31 | 5.84$^{a}$ |
| | (1.54) | (1.43) | (1.47) | (1.42) | (1.84) |
| 'PUGET | 5.84 | 6.10 | 5.71$^{ab}$ | 5.84 | 4.92$^{c}$ |
| RELIANCE' | (1.77) | (1.68) | (1.40) | (1.78) | (1.98) |
| BC 86-33-2 | 5.28 | 6.33 | 6.06$^{a}$ | 6.16 | 5.38$^{b}$ |

TABLE 10-continued (From 1993 progress report to Oregon Strawberry Commission by Brian Yorgey)
Sugared and Sliced Strawberries, 1992–93 Consumer Panel Means, Standard Deviations (in parentheses), Least Significant Difference (LSD) and Significance Level for Flavor and Appearance
(Means with the same superscripts within each column are not significantly different: p ≦ .05.)

| | | | | | |
|---|---|---|---|---|---|
| | (1.49) | (1.58) | (1.52) | (1.50) | (1.72) |
| Totem | 6.26 | 6.35 | 5.88[a] | 6.21 | 5.20[bc] |
| | (1.67) | (1.67) | (1.34) | (1.80) | (1.82) |
| LSD | — | — | .36 | — | .44 |
| Sig. Level | NS | NS | .04 | NS | .001 |

| | | Appearance | | | |
|---|---|---|---|---|---|
| Selection | Overall Appearance | Color | Size | Shape | Seediness |
| 1076-124 | 4.87[bc] | 5.62[b] | 5.95[a] | 5.18[ab] | 5.40[b] |
| | (1.86) | (1.88) | (1.30) | (1.83) | (1.40) |
| 1077-47 | 5.22[ab] | 6.39[a] | 6.07[a] | 4.92[b] | 5.42[b] |
| | (1.71) | (1.37) | (1.46) | (1.78) | (1.41) |
| 1267-236 | 4.63[cd] | 5.89[b] | 4.54[c] | 4.44[c] | 5.24[b] |
| | (2.00) | (1.73) | (1.90) | (1.95) | (1.53) |
| 'PUGET | 4.45[d] | 5.60[b] | 5.57[b] | 4.45[c] | 5.20[b] |
| RELIANCE' | (1.73) | (1.72) | (1.57) | (1.78) | (1.50) |
| BC 86-33-2 | 5.29[a] | 5.70[b] | 6.02[a] | 5.54[a] | 5.78[a] |
| | (1.79) | (1.99) | (1.62) | (1.95) | (1.44) |
| Totem | 5.07[ab] | 6.34[a] | 6.10[a] | 4.88[bc] | 5.31[b] |
| | (1.75) | (1.58) | (1.54) | (1.91) | (1.43) |
| LSD | .41 | .41 | .34 | .44 | .34 |
| Sig. Level | .0002 | .0001 | .0001 | .0001 | .0125 |

'Puget Reliance' did not rate highly for flavor as a fresh strawberry but did for all appearance attributes of IQF fruit. Its flavor was not significantly different from 'Totem' as IQF or sugared and sliced strawberries. The physical and chemical attributes of the new variety are set forth in Table 11 below.

TABLE 11

(From 1993 progress report to Oregon Strawberry Commission by Brian Yorgey)

| selection | date | *Brix | pH | TA | Asc. Acid mc/100 g |
|---|---|---|---|---|---|
| ORUS 1076-124 | 6/2 | 10.2 | 3.38 | 1.33 | 84.1 |
| | 6/11 | 12.5 | 3.28 | 1.26 | 84.2 |
| | 6/18 | 14.2 | 3.44 | 1.22 | 72.5 |
| ORUS 1077-47 | 6/4 | 9.9 | 3.21 | 1.35 | 56.6 |
| | 6/11 | 12.1 | 3.31 | 1.27 | 60.7 |
| | 6/18 | 11.2 | 3.38 | 1.36 | 62.1 |
| ORUS 1267-236 | 5/21 | 10.1 | 3.46 | 1.18 | 80.2 |
| | 5/26 | 10.1 | 3.36 | 1.29 | 85.1 |
| | 6/2 | 10.6 | 3.50 | 1.07 | 61.6 |
| | 6/11 | 13.2 | 3.46 | 1.08 | 73.0 |
| ORUS 1267-314 | 5/26 | 10.4 | 3.54 | 0.93 | 70.0 |
| | 6/2 | display sample only | | | |
| | 6/11 | 14.3 | 3.48 | 1.06 | 76.5 |
| ORUS 1375-24 | 5/19 | 10.1 | 3.45 | 1.00 | 54.4 |
| | 5/26 | 9.7 | 3.53 | 0.95 | 75.5 |
| | 6/11 | 11.5 | 3.62 | 0.85 | 76.9 |
| ORUS 1182-53 | 5/19 | 9.0 | 3.56 | 0.96 | 53.6 |
| ORUS 1182-118 | 5/21 | 8.8 | 3.54 | 0.87 | 71.8 |
| ORUS 1284-79 | 5/19 | 8.7 | 3.36 | 1.10 | 23.6 |
| | 5/26 | 8.9 | 3.28 | 1.18 | 56.5 |
| ORUS 1274-9 | 5/19 | 9.7 | 3.55 | 0.96 | 84.7 |
| ORUS 1376-16 | 5/21 | 9.6 | 3.34 | 1.31 | 100.1 |
| NW8808-79 | 5/21 | 8.2 | 3.57 | 0.88 | 71.3 |
| W84025-26 | 5/26 | 9.2 | 3.61 | 0.94 | 103.8 |
| W87010-7P | 5/26 | 9.1 | 3.38 | 1.08 | 99.9 |
| W88017-49 | 6/4 | 9.1 | 3.33 | 1.24 | 59.4 |

TABLE 11-continued (From 1993 progress report to Oregon Strawberry Commission by Brian Yorgey)

| | | | | | |
|---|---|---|---|---|---|
| W88127-73 | 5/21 | 9.3 | 3.62 | 0.85 | 72.0 |
| W88128-51 | 6/4 | display sample only | | | |
| BC 86-33-2 | 5/26 | 12.1 | 3.40 | 1.40 | 82.5 |
| | 6/2 | 12.5 | 3.53 | 1.14 | 62.8 |
| WSU 2009 (WA) | 6/4 | 6.8 | 3.32 | 0.71 | 37.3 |
| WSU 2068 (WA) | 6/4 | 7.0 | 3.30 | 0.98 | 63.7 |
| 'PUGET RELIANCE' | 6/4 | 8.4 | 3.25 | 1.05 | 54.1 |
| 'PUGET RELIANCE' | 6/2 | 8.7 | 3.38 | 1.14 | 46.0 |
| (NWREC) | 6/4 | 8.2 | 3.20 | 1.06 | 46.6 |
| Totem | 5/19 | 9.9 | 3.48 | 1.00 | 78.4 |
| | 5/26 | 10.0 | 3.45 | 1.12 | 106.8 |
| | 6/2 | 10.8 | 3.58 | 0.96 | 73.7 |
| | 6/4 | 9.7 | 3.50 | 0.92 | 72.9 |
| Redcrest | 6/4 | display sample only | | | |
| | 6/11 | display sample only | | | |
| Hood | 6/2 | display sample only | | | |
| Benton | 6/4 | display sample only | | | |

| selection | date | penetremeter | L | a | b |
|---|---|---|---|---|---|
| ORUS 1076-124 | 6/2 | 529 | 29.48 | 23.15 | 8.03 |
| | 6/11 | 479 | 28.91 | 22.99 | 7.48 |
| | 6/18 | 417 | 27.85 | 20.59 | 6.46 |
| ORUS 1077-47 | 6/4 | 366 | 29.12 | 22.72 | 8.08 |
| | 6/11 | 354 | 28.72 | 21.97 | 7.45 |
| | 6/18 | 395 | 28.22 | 21.33 | 7.48 |
| ORUS 1267-236 | 5/21 | 373 | 30.23 | 21.98 | 7.78 |
| | 5/26 | 388 | 29.70 | 22.31 | 8.06 |
| | 6/2 | 403 | 27.54 | 19.16 | 6.55 |
| | 6/11 | 307 | 29.93 | 20.70 | 7.05 |
| ORUS 1267-314 | 5/26 | 389 | 30.24 | 20.64 | 7.37 |
| | 6/2 | | | | |
| | 6/11 | 346 | 30.05 | 19.61 | 6.41 |
| ORUS 1375-24 | 5/19 | 474 | 29.90 | 21.05 | 7.26 |
| | 5/26 | 465 | 30.90 | 21.95 | 7.60 |
| | 6/11 | 377 | 30.20 | 19.04 | 5.93 |
| ORUS 1182-53 | 5/19 | 413 | 27.97 | 19.59 | 6.50 |
| ORUS 1182-118 | 5/21 | 324 | 29.24 | 20.22 | 7.11 |
| ORUS 1284-79 | 5/19 | 334 | 31.61 | 21.08 | 8.14 |
| | 5/26 | 323 | 31.57 | 22.83 | 8.83 |
| ORUS 1274-9 | 5/19 | 382 | 28.28 | 19.82 | 6.72 |
| ORUS 1376-16 | 5/21 | 458 | 26.75 | 18.11 | 6.15 |
| NW8808-79 | 5/21 | 364 | 29.14 | 19.58 | 6.70 |
| W84025-26 | 5/26 | 434 | 26.09 | 16.88 | 5.24 |
| W87010-7P | 5/26 | 523 | 24.14 | 13.74 | 4.29 |
| W88017-49 | 6/4 | 336 | 29.70 | 21.91 | 7.70 |
| W88127-73 | 5/21 | 351 | 28.38 | 19.56 | 6.50 |
| W88128-51 | 6/4 | | | | |
| BC 86-33-2 | 5/26 | 390 | 27.70 | 20.14 | 6.94 |
| | 6/2 | 419 | 27.55 | 20.20 | 6.72 |
| WSU 2009 (WA) | 6/4 | 458 | 27.65 | 18.04 | 6.40 |
| WSU 2068 (WA) | 6/4 | 531 | 28.92 | 20.76 | 7.33 |
| 'PUGET RELIANCE' | 6/4 | 377 | 29.43 | 21.31 | 7.95 |
| 'PUGET RELIANCE' | 6/2 | 316 | 27.82 | 19.83 | 7.08 |
| (NWREC) | 6/4 | 343 | 29.99 | 21.29 | 8.03 |
| Totem | 5/19 | 320 | 27.28 | 18.91 | 6.46 |
| | 5/26 | 343 | 27.89 | 20.42 | 7.12 |
| | 6/2 | 367 | 27.54 | 19.16 | 6.55 |
| | 6/4 | 295 | 27.17 | 18.66 | 6.17 |
| Redcrest | 6/4 | | | | |
| | 6/11 | | | | |
| Hood | 6/2 | | | | |
| Benton | 6/4 | | | | |

Analysis of frozen samples of the fruit of 'Puget Reliance' taken from the 1992 season at Puyallup appear in Table 12 below.

TABLE 12

Analysis of 1992 strawberry fruit grown at Puyallup, WA.

| | Number of sample | pH | Titratable Acidity as % Citric Acid |
|---|---|---|---|

TABLE 12-continued

Analysis of 1992 strawberry fruit grown at Puyallup, WA.

| | | | |
|---|---|---|---|
| ANNAPOLIS | 1 | 3.56 | 0.21 |
| BC 86-33-2 | 3 | 3.47 A–B | 0.63 B–C |
| CAVENDISH | 1 | 3.72 | 0.51 |
| MDUS 4740 | 1 | 3.41 | 0.57 |
| REDCREST | 3 | 3.24 C | 0.87 A |
| SUMAS-1990 | 3 | 3.34 B–C | 0.37 D |
| SUMAS-1991 | 3 | 3.47 A–B | 0.58 B–D |
| TOTEM-1990 | 3 | 3.48 A–B | 0.42 C–D |
| TOTEM-1991 | 3 | 3.57 A | 0.42 C–D |
| 'PUGET RELIANCE' | 3 | 3.27 C | 0.70 A–B |
| WSU 1990 | 2 | 3.43 | 0.38 |
| WSU 2068 | 2 | 3.42 | 0.45 |
| WSU 2122 | 1 | 3.42 | 0.62 |
| WSU 2212 | 3 | 3.48 A–B | 0.58 B–D |
| WSU 2213 | 3 | 3.53 A | 0.56 B–D |
| Average | | 3.45 | 0.52 |

| | Number of sample | S.S. % | Anthocyanins A @ 520 nm 10 g fr in 1000 ml |
|---|---|---|---|
| ANNAPOLIS | 1 | 7.80 | 0.350 |
| BC 86-33-2 | 3 | 9.60 A | 0.372 A |
| CAVENDISH | 1 | 10.20 | 0.380 |
| MDUS 4740 | 1 | 7.60 | 0.197 |
| REDCREST | 3 | 8.63 A–C | 0.410 A |
| SUMAS-1990 | 3 | 8.03 B–D | 0.358 A |
| SUMAS-1991 | 3 | 9.27 A–B | 0.296 A |
| TOTEM-1990 | 3 | 6.27 E | 0.396 A |
| TOTEM-1991 | 3 | 8.73 A–C | 0.358 A |
| 'PUGET RELIANCE' | 3 | 7.80 C–D | 0.325 A |
| WSU 1990 | 2 | 6.70 | 0.432 |
| WSU 2068 | 2 | 7.25 | 0.424 |
| WSU 2122 | 1 | 9.40 | 0.309 |
| WSU 2212 | 3 | 6.97 D–E | 0.397 A |
| WSU 2213 | 3 | 7.03 D–E | 0.375 A |
| Average | | 8.09 | 0.359 |

Means of samples of 10 grams for each clone.
Means followed by the same letter within a column are not significantly different using Duncan's Multiple Range Test, P = 0.05.

It was concluded that fruit of 'Puget Reliance' would be satisfactory as a processed strawberry and under the standard Washington State University Test Agreement (a copy of which is made of record), one hundred twenty-five virus infected plants were sent to each of four growers in Washington and Oregon. Despite the poor plant quality and low survival at several sites, the fruit produced was received favorably. Six hundred virus negative plants were then sent to one grower and four hundred plants to another in 1993 and these also tested favorably.

Throughout the testing of 'Puget Reliance' at research facilities in Oregon, Washington and British Columbia the variety displayed consistently high yields and large fruit.

The specific morphological characteristics which distinguish 'Puget Reliance' from other Pacific Northwest cultivars are set forth in Tables 13, 14 and 15. These concern the length, width and serration numbers of the central leaflet, the Petiolule and Petiole length and diameters and the length, width and color of the fruit as compared with closely related known varieties.

SPECIFIC DESCRIPTION

The color terminology is in accordance with the Munsell color system.

Plant: Large and vigorous, with an erect growth habit. Produces abundant runners.

Leaves: Medium in size. Leaf characteristics of 'Puget Reliance' are compared to other Pacific Northwest varieties in Table 13. The central leaflet of 'Puget Reliance' is longer than 'Benton' or 'Totem' and the same as 'Sumas'. The width of 'Puget Reliance' is the same as 'Benton' and 'Totem' and narrower than 'Sumas'. The shape of the central leaflet is much longer and narrower for 'Puget Reliance' than for 'Benton', 'Sumas' or 'Totem' as indicated by greater length/width ratio. The number of serrations on the terminal leaflet for 'Puget Reliance' were less than for 'Sumas' but did not differ from 'Benton' or 'Totem'. 'Puget Reliance' had a long petiolule similar in length to 'Sumas'. The petiole length is similar for 'Puget Reliance,' 'Benton' and 'Sumas' but longer than 'Totem'. The leaf color is the same for all four varieties, 5GY 4/4 on the upper surface and 5GY 5/4 for the lower surface. The petiole hairs are irregularly perpendicular to the axis of the petiole.

Inflorescence: Inflorescence characteristics of 'Puget Reliance' are compared to other Pacific Northwest varieties in Table 14. The common peduncle of 'Puget Reliance' is the same as 'Totem' and shorter than 'Benton' or 'Sumas'. The length of the pedicel is similar to 'Benton', but shorter than 'Sumas' and longer than 'Totem'. The diameter of the pedicel is similar to 'Benton' and thicker than 'Sumas' and 'Totem'. The pedicel hairs are irregularly perpendicular to the axis of the pedicel.

Fruit: Fruit characteristics of 'Puget Reliance' are compared to Pacific Northwest varieties in Table 15. The primary fruit of all four varieties is approximately 4 cm. The diameter of 'Puget Reliance' fruit is larger resulting in a shorter conic fruit. Fruit is usually smooth and symmetrically conic with inserted seeds. The exterior fruit color of 'Puget Reliance' (5R 3/6) and 'Totem' (5R 3/6) is slightly darker than 'Benton' and 'Sumas' (5R 3/9). As shown in Table 15, the fruit color at the apex of a longitudinal slice of both 'Puget Reliance' and 'Totem' is darker than for 'Benton' and 'Sumas'. The harvest season is the same as 'Totem', later than 'Hood' or 'Sumas' and earlier than 'Benton'.

Disease and pest reaction: 'Puget Reliance' is susceptible to strawberry aphid (*Chaetosiphon fragaefolii*) an aphid vector of viruses, but is highly tolerant to virus complexes common in Washington. It is susceptible to leaf scorch (Diplocarpon), anthracnose fruit rot (Collectotrichum), and is susceptible to both adult and larva root weevils in a field with both black vine weevil (*Otiorhynchus sulcatus*) and obscure room weevil (*Sciopithes obscurus*).

TABLE 13

Leaf characteristics of 'Puget Reliance', 'Benton', 'Sumas', and 'Totem'. Puyallup, WA (June 29, 1994)

| | Central Leaflet | | | |
|---|---|---|---|---|
| | Length cm | Width cm | Length/ width | Serration Number |
| 'Puget Reliance' | 8.46 a | 6.68 b | 1.27 | 20.0bc |
| 'Benton' | 6.89 b | 6.34 b | 1.09 | 18.6 c |
| 'Sumas' | 9.14 a | 8.33 a | 1.10 | 24.3 a |
| 'Totem' | 6.54 b | 6.06 b | 1.08 | 21.3 b |

| | Petiolule Length mm | Petiole Length cm |
|---|---|---|
| 'Puget Reliance' | 15.5a | 20.9 a |
| 'Benton' | 6.1b | 21.8 a |
| 'Sumas' | 12.1a | 21.4 a |

TABLE 13-continued

Leaf characteristics of 'Puget Reliance', 'Benton', 'Sumas', and 'Totem'. Puyallup, WA (June 29, 1994)

| | | |
|---|---|---|
| 'Totem' | 7.8b | 13.2 b |

TABLE 14

Inflorescence characteristics of 'Puget Reliance', 'Benton', 'Sumas', and 'Totem'. Puyallup, WA (June 22, 1994)

| | Peduncle | | Pedicel | |
|---|---|---|---|---|
| | length cm | diameter mm | length cm | diameter mm |
| 'Puget Reliance' | 15.1 b | 2.52 | 4.24 b | 1.77 a |
| 'Benton' | 20.4 a | 2.35 | 4.44 b | 1.56 a |
| 'Sumas' | 20.9 a | 2.50 | 7.16 a | 1.14 b |
| 'Totem' | 15.6 b | 2.04 | 2.75 c | 1.02 b |

TABLE 15

Fruit characteristics of 'Puget Reliance', 'Benton', 'Sumas', and 'Totem'. Puyallup, WA (Color measured on June 11, 1992 other measurements June 22, 1994)

| | Fruit | | | | | Calyx |
|---|---|---|---|---|---|---|
| | Length cm | Width cm | Length/ width | External color | Internal color | diameter cm |
| 'Puget Reliance' | 4.08 | 3.50 a | 1.15 | 5R 3/6 | 7.5R 4/9 | 3.00 |
| 'Benton' | 3.64 | 2.98 b | 1.22 | 5R 3/9 | 10R 5/10 | 2.89 |
| 'Sumas' | 3.87 | 3.13 b | 1.24 | 5R 3/9 | 10R 5/10 | 2.70 |
| 'Totem' | 3.75 | 2.97 b | 1.29 | 5R 3/6 | 7.5R 5/10 | 2.93 |

I claim:

1. The new and distinct variety of strawberry plant described and illustrated and identified by the characteristics enumerated above.

* * * * *